United States Patent
Mohammadi et al.

(10) Patent No.: US 10,676,556 B2
(45) Date of Patent: *Jun. 9, 2020

(54) WATER-ABSORBING (METH) ACRYLIC RESIN WITH OPTICAL EFFECTS, AND RELATED COMPOSITIONS

(71) Applicants: ELC Management LLC, Melville, NY (US); Shin-Etsu Chemical Co., Ltd., Tokyo (JP)

(72) Inventors: Fatemeh Mohammadi, Hauppauge, NY (US); Lisa Qu, Flushing, NY (US); Emi Akabane, Annaka (JP)

(*) Notice: Subject to any disclaimer, the term of this patent is extended or adjusted under 35 U.S.C. 154(b) by 0 days.

This patent is subject to a terminal disclaimer.

(21) Appl. No.: 15/348,544

(22) Filed: Nov. 10, 2016

(65) Prior Publication Data

US 2018/0127529 A1 May 10, 2018

Related U.S. Application Data

(63) Continuation of application No. 14/450,557, filed on Aug. 4, 2014, now Pat. No. 9,616,253.

(51) Int. Cl.

| C08F 290/06 | (2006.01) |
|---|---|
| C08G 77/20 | (2006.01) |
| C08G 77/14 | (2006.01) |
| A61Q 19/00 | (2006.01) |
| A61K 8/896 | (2006.01) |
| C08G 77/04 | (2006.01) |
| C08F 230/02 | (2006.01) |
| C08G 77/46 | (2006.01) |
| C08F 130/02 | (2006.01) |
| C08L 83/12 | (2006.01) |

(52) U.S. Cl.
CPC .......... *C08F 290/068* (2013.01); *A61K 8/896* (2013.01); *A61Q 19/00* (2013.01); *C08F 230/02* (2013.01); *C08G 77/04* (2013.01); *C08G 77/20* (2013.01); *C08G 77/46* (2013.01); *A61K 2800/10* (2013.01); *A61K 2800/48* (2013.01); *C08F 130/02* (2013.01); *C08G 77/045* (2013.01); *C08G 77/14* (2013.01); *C08L 83/12* (2013.01)

(58) Field of Classification Search
CPC ...... C08F 230/02; C08F 130/02; C08F 77/04; C08F 77/045; C08F 77/20; C08F 77/14; C08F 77/46; C08F 290/068; C08L 83/12; C08L 83/06; C08G 77/04; C08G 77/045; C08G 77/20; C08G 77/14; C08G 77/46

See application file for complete search history.

(56) References Cited

U.S. PATENT DOCUMENTS

| 7,999,051 | B2* | 8/2011 | Stopek | A01N 43/08 424/422 |
|---|---|---|---|---|
| 2008/0009600 | A1 | 1/2008 | Lu et al. | |
| 2009/0021697 | A1* | 1/2009 | Burles | A61B 3/125 351/219 |
| 2012/0136087 | A1* | 5/2012 | Parakka | A61L 15/26 523/107 |
| 2012/0220689 | A1* | 8/2012 | Yao | G02B 1/043 523/107 |
| 2012/0220744 | A1* | 8/2012 | Liu | G02B 1/043 526/279 |
| 2014/0109836 | A1 | 4/2014 | Gauker et al. | |
| 2014/0193351 | A1 | 7/2014 | Mohammadi et al. | |

FOREIGN PATENT DOCUMENTS

| EP | 1310262 A1 | 5/2003 |
|---|---|---|
| EP | 2662400 | 11/2013 |
| JP | 10177152 A * | 6/1998 |
| JP | 2016169327 A * | 9/2016 |
| WO | WO-2011/107478 | 9/2011 |
| WO | WO-2011/127311 | 10/2011 |

OTHER PUBLICATIONS

Shimizu, Takanori et al, "Super-hydrophilic silicone hydrogels with interpenetrating poly(2-methacryloyloxyethyl phosphorylcholine) networks", Feb. 1, 2010, vol. 31 Issue 12 p. 3274-3280.*

International Cosmetic Ingredient Dictionary and Handbook, 2012; Fourteenth Edition vol. 2; p. 2481.

Supplementary European Search Report; 15829864.6; Completion Date: Dec. 12, 2017; dated Dec. 20, 2017.

CN Search Report; Applic No. 201580041712.0; Completion Date: Nov. 27, 2018; dated Jan. 21, 2019.

* cited by examiner

*Primary Examiner* — Ling Siu Choi
*Assistant Examiner* — David L Miller
(74) *Attorney, Agent, or Firm* — Julie M. Blackburn; Sonsy P. Rajan

(57) ABSTRACT

A water-absorbing polymer obtained from polymerization of (A) and (B) in aqueous medium wherein (A) is a phosphate-containing (meth)acrylic monomer and/or a salt thereof, and (B) is a monomer having one (meth)acrylic group within the molecule and/or a salt thereof that is different from component (A); and reacting the reaction product of (A) and (B) with (C) an organopolysiloxane having a (meth)acrylic group at both ends.

19 Claims, 2 Drawing Sheets

Photographs taken after 2 minutes

Photographs taken after 2 hours

Invention Composition

Comparative #1

Comparative #2

Comparative #3

WATER-ABSORBING (METH) ACRYLIC RESIN WITH OPTICAL EFFECTS, AND RELATED COMPOSITIONS

TECHNICAL FIELD

This invention relates to a water-absorbing (meth) acrylic resin, and a skin external preparation comprising the same suitable as cosmetics.

BACKGROUND ART

In the field of skin external preparations including cosmetics and skin external drugs, water-absorbing polymers are used in aqueous cosmetics and aqueous skin external drugs as a thickening/gelling agent for stabilizing the system. The water-absorbing polymers, however, have the drawback that they give an unpleasant slimy feel on use. This is because the polymer forms a gel network structure, which is stable and thus difficult to break down on use. Because of the unpleasant feel, sometimes the use of the cosmetic or drug must be interrupted. While it is desired to solve the problem, non-silicone water-absorbing polymers are unsatisfactory. See Patent Document 1.

To solve the drawback of an aqueous skin external preparation using a water-absorbing polymer, Patent Documents 2 and 3 propose water-absorbing polymers having a silicone structure incorporated therein and cosmetic compositions comprising the same. These water-absorbing polymers still have problems including difficult control of three-dimensional structure due to cross linking of epoxy groups, and a change with time of water absorption capability.

Thus, it is desirable to create water absorbing polymers that provide optimal aesthetics as well as to provide other desirable cosmetic properties. If an ingredient used to formulate cosmetic products can multiple functions, this means fewer ingredients can be used in the formulation which reduces cost and the potential for adverse interactions between ingredients.

Particularly in cosmetic applications, it is very desirable to create a film on skin that blurs skin defects such as lines, wrinkles, or minor skin imperfections. In addition to provide aesthetically pleasing thickening properties, when the same polymers provide other benefits such as optically improving the appearance of the skin surface this provides a further advantage.

CITATION LIST

Patent Document 1: JP-A 2000-327516
Patent Document 2: WO 2007/130412
Patent Document 3: WO 2007/130460

SUMMARY OF INVENTION

An object of the invention is to provide a cosmetic composition which exerts a high thickening effect in aqueous solvents, eliminates poor spreading, moist and sticky feels, and is in paste form having thixotropy and giving a dry light feel.

Another object of the invention is to provide a cosmetic composition containing such polymer, which also provides optical effects on skin such as blurring the appearance of skin imperfections and providing the visual appearance of smooth, homogeneously colored skin.

The inventors have found that using a water-absorbing polymer defined herein, a skin external composition is formulated that can attain the above objectives and other objects.

DESCRIPTION OF PREFERRED EMBODIMENTS

Figure 1:
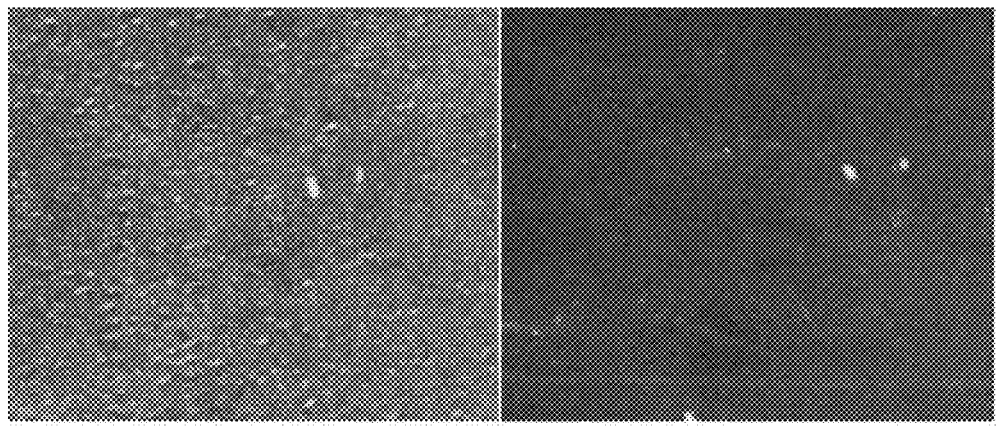
FIG. 1 shows photographs taken at two minutes of glass slides onto which the invention and comparative compositions were applied according to the procedure in Example 2.
Figure 1:
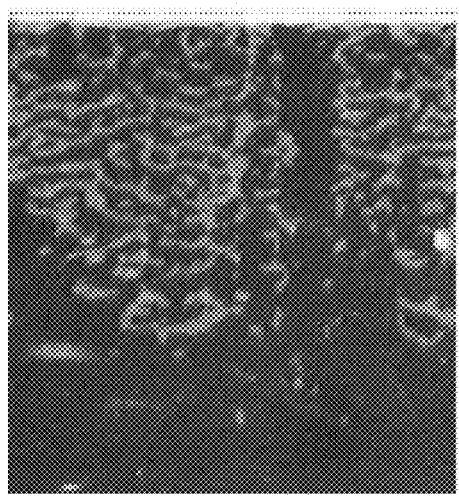
Figure 1:

Component (A) is a phosphate-containing (meth)acrylic monomer. As long as a monomer has a phosphate group and a (meth)acrylic group, the structure of a linkage for connecting these two groups is not particularly limited. Exemplary linkages include alkylene groups such as methylene, ethylene and propylene and oxyalkylene groups such as oxyethylene, oxypropylene, oxybutylene, oxypentamethylene and mixtures thereof. Of these, polyoxyalkylene groups are preferred, with polyoxypropylene being most preferred. The monomer is commercially available, for example, under the tradename of Sipomer PAM-200 from Rhodia.

Also included is a salt of a phosphate-containing (meth) acrylic monomer, which may be formed by adding an alkaline aqueous solution to the phosphate-containing (meth)acrylic monomer.

Component (B) is a monomer having one (meth)acrylic group within the molecule other than component (A). Suitable (meth)acrylic monomers include (meth)acrylic acid, maleic acid, maleic anhydride, fumaric acid, crotonic acid, itaconic acid, 2-(meth)acrylamide-2-methylpropanesulfonic acid, (meth)acryloxyalkanesulfonic acid, N-vinyl-2-pyrrolidone, N-vinylacetamide, (meth)acrylamide, N-isopropyl (meth)acrylate, N,N-dimethyl(meth)acrylamide, 2-hydroxyethyl (meth)acrylate, methoxypolyethylene glycol (meth) acrylate, polyethylene glycol (meth)acrylate, and strearyl acrylate. A salt of the (meth)acrylic monomer may be formed by adding an alkaline aqueous solution to the (meth)acrylic monomer.

The "salt" includes alkali metal salts such as sodium, potassium and lithium, alkaline earth metal salts such as calcium, magnesium and barium, and ammonium salts such as quaternary ammonium and quaternary alkyl ammonium. Inter alia, sodium salt is the most common and preferred. Neutralization treatment is preferably carried out at a temperature of 10 to 100° C., more preferably 20 to 90° C. Acrylic acid or polyacrylic acid following polymerization may be neutralized with a base. Neutralization prior to polymerization is preferred because it is time consuming to post-neutralize non-neutralized or low-neutralized (specifically a degree of neutralization of less than 30 mol %) polyacrylic acid following polymerization. The water-absorbing polymer of the invention preferably has a degree of neutralization of 0.01 to 100%, more preferably 1 to 90%, and even more preferably 20 to 80% based on the moles of acid groups in the polymer.

Component (C) is an organopolysiloxane having a (meth) acrylic group at both ends, represented by the general formula (1).

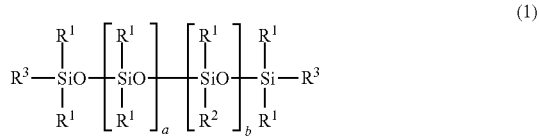
(1)

Herein $R^1$ is each independently an aliphatic unsaturation-free monovalent hydrocarbon group having 1 to 8 carbon atoms. $R^2$ is a group containing a polyoxyalkylene group having the general formula (2):

$$-R^4(OC_2H_4)x(OC_3H_6)yOH \quad (2)$$

wherein $R^4$ is each independently a divalent organic group having 2 to 15 carbon atoms, x and y each are an integer of 0 to 30, meeting $1 \leq x+y \leq 50$. $R^3$ is a substituent group having a (meth)acrylic group, a is an integer inclusive of 0 and b is an integer of at least 1.

Examples of the monovalent hydrocarbon group represented by $R^1$ include alkyl groups such as methyl, ethyl and butyl, cycloalkyl groups such as cyclopentyl and cyclohexyl, aryl groups such as phenyl and tolyl, and aralkyl groups such as benzyl and phenethyl. Inter alia, alkyl groups of 1 to 4 carbon atoms and phenyl are preferred, with methyl being most preferred.

In formula (2), $R^4$ is each independently selected from divalent organic groups having 2 to 15 carbon atoms, for example, $-(CH_2)_2-$, $-(CH_2)_3-$, $-(CH_2)_4-$, $-CH_2CH(CH_3)CH_2-$, $-(CH_2)_8-$, and $-(CH_2)_{11}-$. Inter alia, $-(CH_2)_2-$, $-(CH_2)_3-$, and $-(CH_2)_4-$ are preferred. Each of x and y is an integer of 0 to 30, meeting $1 \leq x+y \leq 50$. Preferably each of x and y is an integer of 5 to 25, more preferably 10 to 20, and the sum of x+y is 10 to 45, more preferably 20 to 40.

In the water-absorbing polymer, the phosphate-containing (meth)acrylic monomer and/or salt (A) is preferably present in a content of 30 to 95% by weight. A polymer containing less than 30% by weight of monomer (A) may be less water absorptive whereas a polymer containing more than 95% by weight of monomer (A) may not become pasty after water absorption. The content of monomer (A) is more preferably 40 to 95% by weight, and even more preferably 50 to 80% by weight. Also preferably, the (meth)acrylic monomer and/or salt (B) is present in a content of 4 to 50% by weight, more preferably 15 to 50% by weight, and the organopolysiloxane (C) is present in a content of 0.01 to 20% by weight, more preferably 2 to 20% by weight.

The water-absorbing polymer may be prepared typically by radical polymerization reaction. Although the procedure is not particularly limited, the polymer may be prepared, for example, by diluting monomers (A) and (B) with a solvent, optionally adding an alkali, and polymerizing the monomers with siloxane (C) in the presence of (D) a radical initiator.

The radical polymerization mode for preparing the water-absorbing polymer is not particularly limited. While bulk polymerization and precipitation polymerization are acceptable, reverse phase suspension polymerization, spray or dropwise polymerization, and aqueous polymerization, especially continuous aqueous polymerization are preferred for polymer performance and ease of polymerization control.

A dispersant may be used during polymerization. Suitable dispersants include cationic and ampholytic surfactants such as sorbitan fatty acid esters and carboxymethyldimethylcetyl ammonium, anionic surfactants such as sodium salt of polyoxyethylene dodecyl ether hydrogensulfate, and polymeric dispersants such as cellulose esters, maleic polybutadiene, and quaternary salt of isopropyl methacrylate-dimethylaminoethyl methacrylate. These dispersants may be used alone or in admixture of two or more. The amount of the dispersant used is preferably 0.01 to 5 parts by weight per 100 parts by weight of the monomer charge. In the case of reverse phase suspension polymerization, an ionic surfactant is preferably used to disperse the monomers because it is also effective for preventing agglomeration of highly water-absorbing resin particles.

The polymerization initiator which can be used in the synthesis of the water-absorbing polymer may be selected depending on the polymerization mode. Examples of the polymerization initiator include photo-decomposable initiators, thermally decomposable initiators, and redox initiators. The amount of the polymerization initiator used is typically 0.001 to 10 mol %, preferably 0.001 to 5 mol % based on the monomer charge. Outside the range, an excess of the initiator may cause coloring or an offensive odor whereas a less amount may lead to an increased amount of residual monomers.

Examples of the photo-decomposable polymerization initiators include benzoin derivatives, benzyl derivatives, acetophenone derivatives, benzophenone derivatives and azo compounds. Examples of the thermally decomposable polymerization initiators include persulfates such as sodium persulfate, potassium persulfate, and ammonium persulfate, peroxides such as hydrogen peroxide, t-butyl peroxide, and methyl ethyl ketone peroxide, azo compounds such as 2,2'-azobis(2-amidinopropane)dihydrochloride and 2,2'-azobis[2-(2-imidazolin-2-yl)propane)dihydrochloride, and perchlorates such as potassium perchlorate and sodium perchlorate. Examples of the redox polymerization initiators include combinations of the above persulfates or peroxides with reducing compounds such as sulfites, L-ascorbic acid or ferrous salts. It is also possible to use the photo-decomposable initiator and thermally decomposable initiator in combination. Among others, the peroxides are preferred for attaining the objects of the invention.

The polymerization initiator may be added all at once or dropwise in the form of a solution. Divided portions of the initiator may be added in the course of reaction.

The polymerization results in a water-absorbing polymer in hydrous gel form, from which the desired water-absorbing resin may be recovered through post-treatment as desired, for example, washing for the purpose of removing any residual monomers and the initiator and drying. For the washing step, any solvent such as water, acetone, alcohols, isoparaffin or volatile silicone may be used, although the solvent is not particularly limited. The solvents may be used alone or in combination, or stepwise for carrying out washing.

The drying step is not particularly limited as long as it is conventional. The preferred modes of drying include heat drying, hot air drying, vacuum drying, IR drying, microwave drying, freeze drying, spray drying, azeotropic drying using hydrophobic organic solvent, and high-humidity drying using hot steam. Hot air drying is more preferred. Although the drying temperature and time are not particularly limited, drying at a high temperature above 150° C. or for a long time of more than 5 hours may give rise to such problems as alternation of the resin, a drop of water absorption factor, and coloring.

If desired, the drying step may be followed by adjustment of particle size or narrowing of particle size distribution via surface crosslinking. The particle size may be adjusted via polymerization, grinding, classification, granulation or fines recovery.

For the surface crosslinking, a surface crosslinking agent is used. Various organic and inorganic surface crosslinking agents are known, with the organic crosslinking agents being preferred. Suitable crosslinking agents are dehydration esterification crosslinkers including polyhydric alcohols, epoxy compounds, polyfunctional amine compounds or condensates thereof with halo-epoxy compounds, oxazoline compounds, and (mono, di or poly)oxazolidinone compounds.

The silicone-crosslinked water-absorbing polymer may take any shape including spherical, mass, flake, plate, oval, fiber, irregular, a compact of consolidated particles and other shapes.

The silicone-crosslinked water-absorbing polymer preferably has an average particle size of 100 nm to 1 mm, more preferably 500 nm to 500 μm, in a state prior to water absorption (i.e., a loss of up to 5% on 150° C./3 hour heating) although the average particle size is not critical.

The silicone-crosslinked water-absorbing polymer functions to convert water solvent into gel. The term "gel" means that the water-absorbing polymer absorbs a low-viscosity liquid so that the liquid may exhibit no or substantially no fluidity. The water solvent may be water alone or a mixture of water and an organic solvent. The organic solvent which is mixed with water is not particularly limited. Among others, amphiphatic solvents are preferred, for example, alcohols such as methanol, ethanol, propanol and 2-propanol, ketones such as acetone, and ethers such as tetrahydrofuran and dioxane.

Another embodiment of the invention is a cosmetic or skin external preparation comprising 0.01 to 60%, preferably from about 0.1 to 20%, more preferably from about 0.1 to 10% by weight (based on the total weight of the preparation) of the water-absorbing polymer defined above.

As used herein, the "skin external preparation" refers to any preparations externally administered to the skin, for example, cosmetics, skin external drugs, skin external disinfectants and bactericides. The term "cosmetic composition" means a composition that is applied to keratin surfaces for purposes of treatment, beautification, or coloration. Better results are obtained when the invention is applied to cosmetics where the feel on use has a large impact on the effect and skin external drugs requiring long-term continuous administration, and especially cosmetics.

The preparation or composition may take the form of lotion, gel, emulsion, cream, powder dispersion, powder dispersion emulsion, or the like. If the composition is in emulsion form, the emulsion may be water-in-oil or oil-in-water. In such case, the composition may comprise from about 2-99% water and from about 1-98% oil.

Various types of cosmetic composition are included, for example, skin care products, foundation make-up cosmetics, and hair care cosmetics.

EXAMPLE

Examples are given below to illustrate the synthesis of water-absorbing polymers and cosmetic compositions using them, but the invention is not limited thereto.

Synthesis Example 1

A 1-L separable flask equipped with a stirrer was charged with 24 g of methacrylic acid, 60 g of Sipomer PMA-200 (Rhodia), and 100 g of deionized water. With stirring, 52 g of 25% sodium hydroxide aqueous solution was added dropwise at 20-30° C. To the solution, 12 g of a methacrylic-terminated siloxane having the following formula (3) was added. With stirring, nitrogen bubbling was continued for 30 minutes, whereupon 100 g of 4% potassium peroxydisulfate aqueous solution was added at 25° C. Thereafter, the flask was heated at 60° C. at which reaction was run for 10 hours. The resulting gel was washed with an excess of acetone/water mixture, filtered, dried in a vacuum dryer for 10 hours, and pulverized in a mill, yielding the desired water-absorbing polymer in white powder particle form.

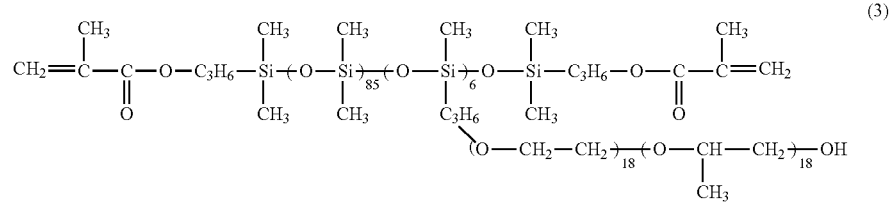

(3)

Synthesis Example 2

A 1-L separable flask equipped with a stirrer was charged with 24 g of methacrylic acid, 60 g of Sipomer PMA-200 (Rohdia), and 110 g of deionized water. With stirring, 52 g of 25% sodium hydroxide aqueous solution was added dropwise at 20-30° C. To the solution, 6 g of a methacrylic-terminated siloxane having the formula (3) was added. With stirring, nitrogen bubbling was continued for 30 minutes, whereupon 50 g of 4% potassium peroxydisulfate aqueous solution and 25 g of 4% sodium hydrogensulfite aqueous solution were added at 25° C. Thereafter, the flask was heated at 50° C. at which reaction was run for 5 hours. The resulting gel was washed three times with an excess of acetone/water mixture, filtered, dried in a vacuum dryer for 10 hours, and pulverized in a mill, yielding the desired water-absorbing polymer in white powder particle form.

Example: Cosmetic Composition

A cosmetic composition containing the polymer of Example 1 was prepared along with comparative formulas, as set forth below.

| Ingredient | Invention Formula | Comparative Formula #1 | Comparative Formula #2 | Comparative Formula #3 |
|---|---|---|---|---|
| Water | QS100 | QS100 | QS100 | QS100 |
| Sodium acrylate crosspolymer-1[1] | 4.00 | | | |
| Sodium Acrylate crosspolymer-2[2] | | 0.30 | | |
| Butylene glycol | 2.0 | 2.0 | 2.0 | 2.0 |
| Sucrose | 0.5 | 0.5 | 0.5 | 0.5 |
| Sorbitol | 0.35 | 0.35 | 0.35 | 0.35 |
| Caprylyl glycol | 0.20 | 0.20 | 0.20 | 0.20 |
| Glucose | 0.05 | 0.05 | 0.05 | 0.05 |
| Disodium EDTA | 0.05 | 0.05 | 0.05 | 0.05 |
| *Laminaria digitata* extract | 0.02 | 0.02 | 0.02 | 0.02 |
| Sodium polyacrylate[3] | | | 0.75 | |
| Carbomer[4] | | | | 0.30 |
| Tromethane | | | | 0.30 |
| Glycerin | 15.00 | 15.00 | 15.00 | 15.00 |

[1]Polymer of Example 1
[2]Aqua Keep 10SH-NFC - Sodium Acrylate Crosspolymer-2. Kobo Products Inc.
[3]Cosmedia SP - Sodium polyacrylate. Cognis Corporation
[4]Carbopol 980 - Carbomer - Momentive Performance Materials The amount of the polymers used initially was adjusted so that the final viscosity of the inventive and comparative formulas was essentially the same to facilitate comparative evaluation, e.g. ranged from 24,000 to 36,000 cps at 25° C.

Figure 2:
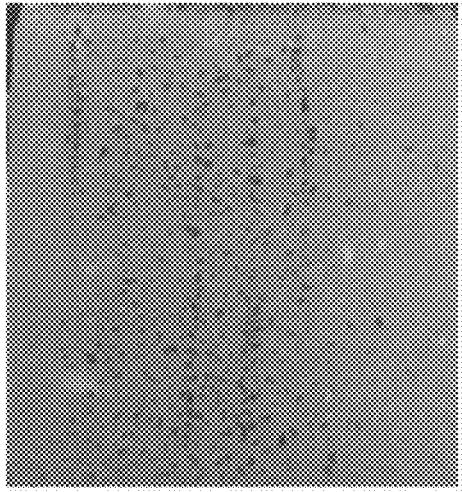
FIG. 2 shows photographs taken at 2 hours of glass slides onto which the invention and comparative compositions were applied according to the procedure in Example 2.
Figure 2:
Figure 2:
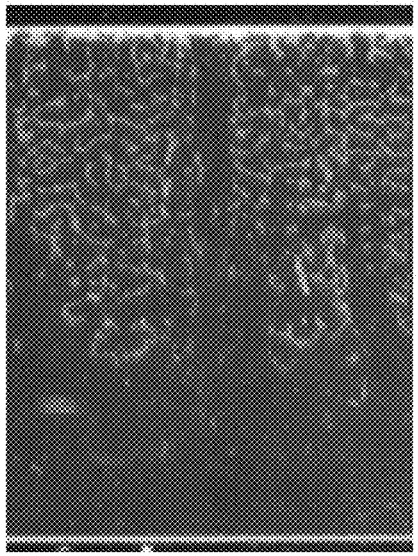
Figure 2:
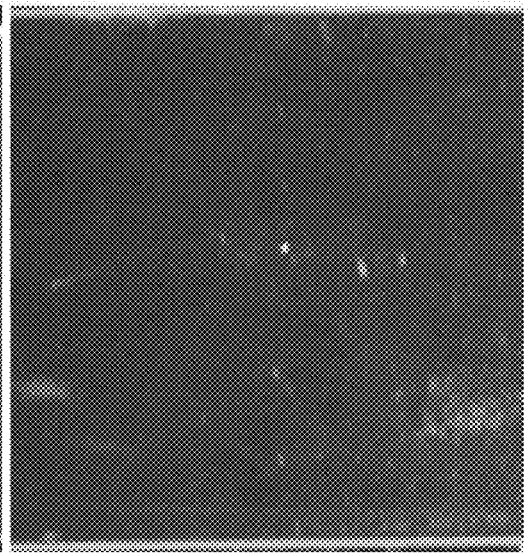

The compositions were tested for ability to optically improve the appearance of surfaces such as skin. 6 mil of each composition was applied to a microscope glass slide using a square applicator. The slides were dried in an air conditioned room at 25° C. The slides were photographed by a Canon PowerShot SD1400 IS camera where images were taken with the slides placed on a black background and the photograph taken at a 45° angle. Photographs were taken at 2 minutes, 2 hours and 24 hours. The results are show in FIGS. 1 and 2. The slides to which the invention composition was applied show an even film that provides a homogeneous light coverage that when visually inspected appears to blur the underlying glass slide. This is confirmed by application to skin with visual observation.

The invention claimed is:

1. A cosmetic composition comprising a water-absorbing polymer obtained from (A) a phosphate-containing (meth)acrylic monomer and/or a salt thereof, (B) a monomer having one acrylic group within the molecule and/or a salt thereof other than component (A), and (C) an organopolysiloxane having an acrylic group at both ends, represented by the general formula (1):

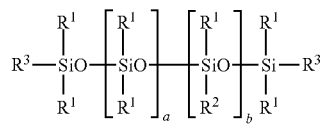

(1)

wherein $R^1$ is each independently an aliphatic monovalent hydrocarbon group having 1 to 8 carbon atoms,
$R^2$ is a group containing a polyoxyalkylene group having the general formula (2):

$$-R^4(OC_2H_4)x(OC_3H_6)yOH \qquad (2)$$

wherein $R^4$ is each independently a divalent organic group having 2 to 15 carbon atoms, x and y each are an integer of 0 to 30, meeting $1 \leq x+y \leq 50$,
$R^3$ is a substituent group having the general formula (4):

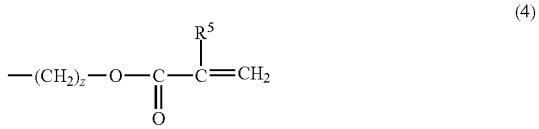

(4)

wherein $R^5$ is H or CH3, z is integer of 1 to 8,
a is an integer inclusive of 0 and b is an integer of at least 1, wherein the water absorbing polymer in form of dried particles have an average particle size of 100 nanometers to 1 millimeter.

2. A cosmetic composition according to claim 1, comprising said water-absorbing polymer obtained from polymerization of (A), (B) and (C) in aqueous medium wherein (A) is a phosphate-containing (meth)acrylic monomer and/or a salt thereof, (B) is a monomer having one acrylic group within the molecule and/or a salt thereof that is different from component (A) and (C) an organopolysiloxane having an acrylic group at both ends, represented by the general formula (1):

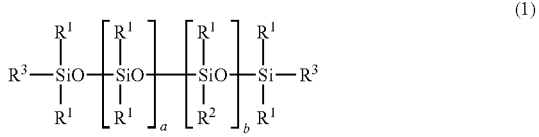

(1)

wherein $R^1$ is each independently an aliphatic monovalent hydrocarbon group having 1 to 8 carbon atoms,
$R^2$ is a group containing a polyoxyalkylene group having the general formula (2):

$$-R^4(OC_2H_4)x(OC_3H_6)yOH \qquad (2)$$

wherein $R^4$ is each independently a divalent organic group having 2 to 15 carbon atoms, x and y each are an integer of 0 to 30, meeting $1 \leq x+y \leq 50$,
$R^3$ is a substituent group having the general formula (4):

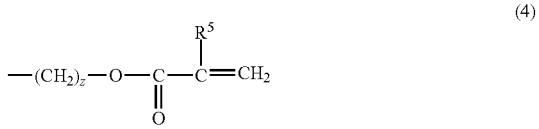

(4)

wherein $R^5$ is H or CH3, z is integer of 1 to 8,
a is an integer inclusive of 0 and b is an integer of at least 1.

3. The cosmetic composition according to claim 2, wherein phosphate containing (meth)acrylic monomer and/or salt (A) contains a phosphate group linked to the (meth) acrylic group by a linking group selected from the group consisting of alkylene, polyalkylene, oxyalkylene, polyoxyalkylene and mixtures thereof.

4. The cosmetic composition according to claim 3, wherein said alkylene linking group is selected from the group consisting of methylene, ethylene, propylene, and mixtures thereof.

5. The cosmetic composition according to claim 3, wherein said polyalkylene linking group is selected from the group consisting of polymethylene, polyethylene, polypropylene, and mixtures thereof.

6. The cosmetic composition according to claim 3, wherein said oxyalkylene linking group is selected from the group consisting of oxyethylene, oxypropylene, oxybutylene, oxypentamethylene, and mixtures thereof.

7. The cosmetic composition according to claim 3, wherein said polyoxyalkylene linking group is selected from the group consisting of polyoxyethylene, polyoxypropylene, polyoxybutylene, polyoxypentamethylene, and mixtures thereof.

8. The cosmetic composition according to claim 7, wherein said polyoxyalkylene linking group is polyoxypropylene.

9. The cosmetic composition according to claim 7, wherein said monomer (A) the phosphate group linked to the (meth)acrylic group by the polyoxyalkylene linking group is present at 30 to 95% by weight.

10. The cosmetic composition according to claim 8, wherein (A) the phosphate containing (meth)acrylic monomer is in the form of a salt.

11. The cosmetic composition according to claim 10, wherein said the salt is sodium or potassium salt of the phosphate-containing (meth)acrylic monomer (A).

12. The cosmetic composition according to claim 1, wherein (B) is an acrylic monomer selected from the group consisting of (meth)acrylic acid, (meth) acrylate, hydroxyethyl (meth)acrylate, stearyl acrylate, and mixtures thereof either alone or in combination with one or more monomers selected from the group consisting of maleic acid, maleic anhydride, fumaric acid, crotonic acid, itaconic acid, 2-(meth)acrylamide-1 methylpropanesulfonic acid and mixtures thereof.

13. The cosmetic composition according to claim 2, wherein said water-absorbing polymer is obtained using 50 to 95% by weight of the phosphate-containing (meth)acrylic monomer and/or salt (A), 4 to 50% by weight of the acrylic monomer and/or salt (B), and 0.01 to 20% by weight of the organopolysiloxane (C).

14. The cosmetic composition according to claim 1, wherein said R1 in component (C) is methyl, ethyl, propyl, or butyl.

15. The cosmetic composition according to claim 14, wherein each of said R4 is independently
—$(CH_2)_2$—, —$(CH_2)_3$—, —$(CH_2)_4$—, —$CH_2CH(CH_3)CH_2$—, —$(CH_2)_8$—, or —$(CH_2)_{11}$—.

16. The cosmetic composition according to claim 15, wherein R4 is —$(CH_2)_2$—, —$(CH_2)_3$—, or —$(CH_2)_4$—.

17. The cosmetic composition according to claim 1, wherein said dried polymer particles have a loss of up to 5% of total weight when heated to a temperature of 150° C. for 3 hours.

18. The cosmetic composition according to claim 1, wherein said (C) has the structure:

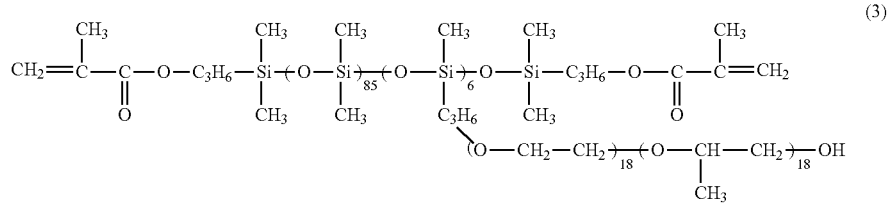

(3)

19. A cosmetic composition comprising a water absorbing polymer which is the reaction product of an aqueous polymerization of methacrylic acid, phosphate esters of Polypropylene glycol monomethacrylate, sodium hydroxide, and an acrylic terminated organosiloxane having the formula:

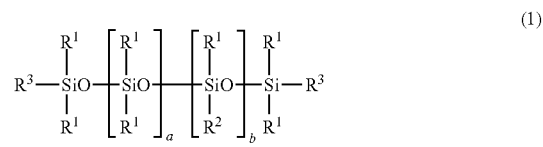

(1)

wherein $R^1$ is methyl, ethyl, propyl, or butyl;
$R^2$ is a group containing a polyoxyalkylene group having the general formula (2):

—$R^4(OC_2H_4)x(OC_3H_6)yOH$   (2)

wherein $R^4$ is —$(CH_2)_2$—, —$(CH_2)_3$—, —$(CH_2)_4$—, —$CH_2CH(CH_3)CH_2$—, —$(CH_2)_8$—, or —$(CH_2)_{11}$—;
and x and y each are an integer of 0 to 30, meeting $1 \leq x+y \leq 50$,
$R^3$ is a substituent group containing a (meth)acrylic group having the general formula (4):

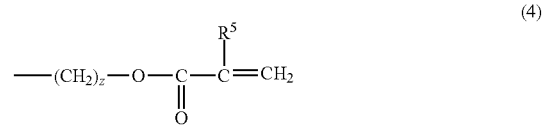

(4)

wherein $R^5$ is H or CH3, z is integer of 1 to 8,
a is an integer inclusive of 0 and b is an integer of at least.

* * * * *